US012582416B2

(12) United States Patent
Parmigiani

(10) Patent No.: US 12,582,416 B2
(45) Date of Patent: Mar. 24, 2026

(54) SURGICAL INSTRUMENT FOR SCRAPING AND COLLECTING BONE PARTICLES

(71) Applicant: META TECHNOLOGIES S.R.L., Reggio Emilia (IT)

(72) Inventor: Corrado Saverio Parmigiani, Correggio (IT)

(73) Assignee: META TECHNOLOGIES S.R.L., Reggio Emilia (IT)

( * ) Notice: Subject to any disclaimer, the term of this patent is extended or adjusted under 35 U.S.C. 154(b) by 291 days.

(21) Appl. No.: 18/259,685

(22) PCT Filed: Jan. 4, 2022

(86) PCT No.: PCT/IB2022/050041
§ 371 (c)(1),
(2) Date: Jun. 28, 2023

(87) PCT Pub. No.: WO2022/149060
PCT Pub. Date: Jul. 14, 2022

(65) Prior Publication Data
US 2024/0050104 A1      Feb. 15, 2024

(30) Foreign Application Priority Data
Jan. 11, 2021    (IT) ........................ 102021000000329

(51) Int. Cl.
*A61B 17/16*          (2006.01)
(52) U.S. Cl.
CPC .................................. *A61B 17/1635* (2013.01)
(58) Field of Classification Search
CPC ................................................. A61B 17/1635
See application file for complete search history.

(56) References Cited

U.S. PATENT DOCUMENTS

2004/0068265 A1*    4/2004    Parmigiani ........ A61B 17/1659
                                                            606/89
2007/0055264 A1*    3/2007    Parmigiani ........ A61B 17/1635
                                                            606/84

FOREIGN PATENT DOCUMENTS

EP          1405602 A1      4/2004
WO       02076307 A1    10/2002
WO    2020115611 A1      6/2020

* cited by examiner

*Primary Examiner* — Andrew Yang
(74) *Attorney, Agent, or Firm* — FisherBroyles, LLP; Roger L. Browdy; Ronni S. Jillions

(57) ABSTRACT

A surgical tool (10) for scraping and collecting bone particles, comprising: —a handle (20) provided with a handgrip (21); —a collection chamber (25) having an end proximal to the handgrip (21) and a free distal end; —a stem (30) at least partially arranged inside the collection chamber (25); —a blade (40) fixed to a front end (32) of the stem (30), wherein the blade (40) protrudes radially from the stem (30) and is axially arranged outside the collection chamber (25) near the distal end thereof; and—a spacer (50) interposed between a rear face (42) of the blade (40) and the distal end of the collection chamber (25), wherein the spacer (50) defines a passage opening (500) for introducing the bone particles scraped by the blade (40) into the collection chamber (25), maintaining at a predetermined non-zero axial distance, for at least a circumferential tract thereof, the rear face (42) of the blade (40) from the distal end of the collection chamber (25).

10 Claims, 4 Drawing Sheets

SURGICAL INSTRUMENT FOR SCRAPING AND COLLECTING BONE PARTICLES

TECHNICAL FIELD

The present invention relates to bone tissue reconstructive and regenerative removal techniques in orthopaedic oro-maxillofacial, plastic, periodontal and implant surgery as well as bone plastic techniques.

More particularly, the present invention relates to a surgical tool for scraping and collecting bone particles, i.e. bone shavings or chips/flakes, which can be used in such tissue regeneration techniques.

PRIOR ART

In the past, tools were developed to harvest bone material from various areas of the skeletal structure with the aim of obtaining granules or particles of a size suitable for tissue biological regenerative needs.

These tools have made it possible to increase autologous bone harvesting techniques and treat the harvested bone material by obtaining bone granules adapted to be inserted into bone pockets to fill bone defects or to increase skeletal structures.

In recent years, harvest methods have been refined by the introduction on the market of tools for removing and collecting particles (chips or shavings), by scraping bones, which comprise a handle carrying a scraping blade at its front end, and a chamber for collecting the removed material.

Among said devices it is included the device disclosed in Patent No. IT1328783 by the same Applicant.

A need perceived in the field is to make such devices increasingly effective and comfortable in scraping and collecting bone chips, as well as to make such devices easier and cheaper to produce, while enabling medical staff to save money.

An object of the present invention is to solve such needs of the prior art, with a simple, rational and cost-effective solution.

These objects are achieved by the features of the invention set forth in the independent claim. The dependent claims outline preferred and/or particularly advantageous aspects of the invention.

DISCLOSURE OF THE INVENTION

The invention, in particular, makes available a surgical tool for scraping and collecting bone particles, comprising:
  a handle provided with a handgrip;
  a collection chamber having an end proximal to the handgrip and a free distal end;
  a stem at least partially arranged inside the collection chamber;
  a blade fixed to distal end of the stem, wherein the blade protrudes radially from the stem and is axially arranged outside the collection chamber near the distal end thereof; and
  a spacer interposed between a rear face of the blade and the distal end of the collection chamber, wherein the spacer defines a passage opening for introducing the bone particles scraped by the blade into the collection chamber, maintaining at a predetermined non-zero axial distance, for at least a circumferential tract thereof, the rear face of the blade from the distal end of the collection chamber.

Thanks to this solution, the construction of the surgical tool, e.g. of the passage opening thereof, and its functionality is particularly improved compared to known surgical tools, as the collection chamber (i.e. the cannula that defines it) does not require any special processing or adaptation, but can be made simply and quickly.

For example, the distal end of the collection chamber can be planar and free from steps or notches, allowing faster, cheaper and more accurate manufacturing.

Advantageously, the spacer can be rigidly attached to the blade and has a first face facing the blade and in contact with it, and a second face facing the distal end of the collection chamber and intended to contact it via a contact portion of the second face.

Thanks to this solution, the coupling between the spacer and the blade (i.e. the stem supporting it) can be made in a simple, constructively rational and efficient way.

According to an aspect of the invention, the spacer may have an annular shape comprising a central hole coaxial with the stem and an asymmetric outer perimeter having a circular portion configured to define a contact portion of the second face, wherein the contact portion is configured to contact the distal end of the collection chamber, and a recess adapted to be radially separated from the distal end of the collection chamber, wherein the passage opening is delimited, in an axial direction, by a portion of a scraping edge of the blade and by a circumferential portion of the distal end of the collection chamber and, in a circumferential direction, by the recess of the spacer.

Thanks to this solution, the spacer is shaped to fulfil in the best possible way its main functions and, at the same time, it can be made quickly and easily using forming techniques suitable for large-scale production.

Advantageously, the collection chamber may have a curved longitudinal extension along a curved line with a single curvature, the passage opening being arranged at an extrados area of the distal end of the collection chamber.

This makes the surgical tool more effective, as it facilitates bone scraping actions, especially in certain circumstances of use, efficient in the collection of bone chips separated from the scraped bone, and comfortable to be used by the personnel in charge of harvesting bone chips.

According to an advantageous aspect of the invention, the stem can be elastically flexible.

Alternatively or additionally, the stem can be elastically extendible, i.e. elongatable.

Thanks to this solution, the elastic reaction of the stem is such that it improves the (impulsive) cutting action of the blade on the bone chips, improving the detachment of the chips from the bone and collection thereof in the collection chamber, while reducing at the same time the side effects generated by the detachment of the chips on the scraped bone (such as lacerations, pain or trauma).

Preferably, the collection chamber and the stem are mutually movable sliding between a collection position of the collection chamber, wherein the second face of the spacer is in contact with the distal end of the collection chamber and the collection chamber is accessible only by the passage opening defined by the spacer, and a discharge position, wherein the second face of the spacer is distal from the distal end of the collection chamber releasing it.

This solution makes it possible to collect and discharge bone chips easily and safely for the staff.

Advantageously, the surgical tool may comprise a locking element configured to temporarily lock the stem and the collection chamber at least in their collection position.

Thanks to this solution, when the surgical tool is in the operative configuration, where the stem and the collection chamber are in their collection position, any accidental opening of the collection chamber is prevented, thus eliminating any risk of loss of the collected bone material or any contamination.

BRIEF DESCRIPTION OF THE DRAWINGS

Further features and advantages of the invention will be more apparent after reading the following description provided by way of non-limiting example, with the aid of the accompanying drawings.

BEST MODE TO IMPLEMENT THE INVENTION

Figures 1, 1A, 5:
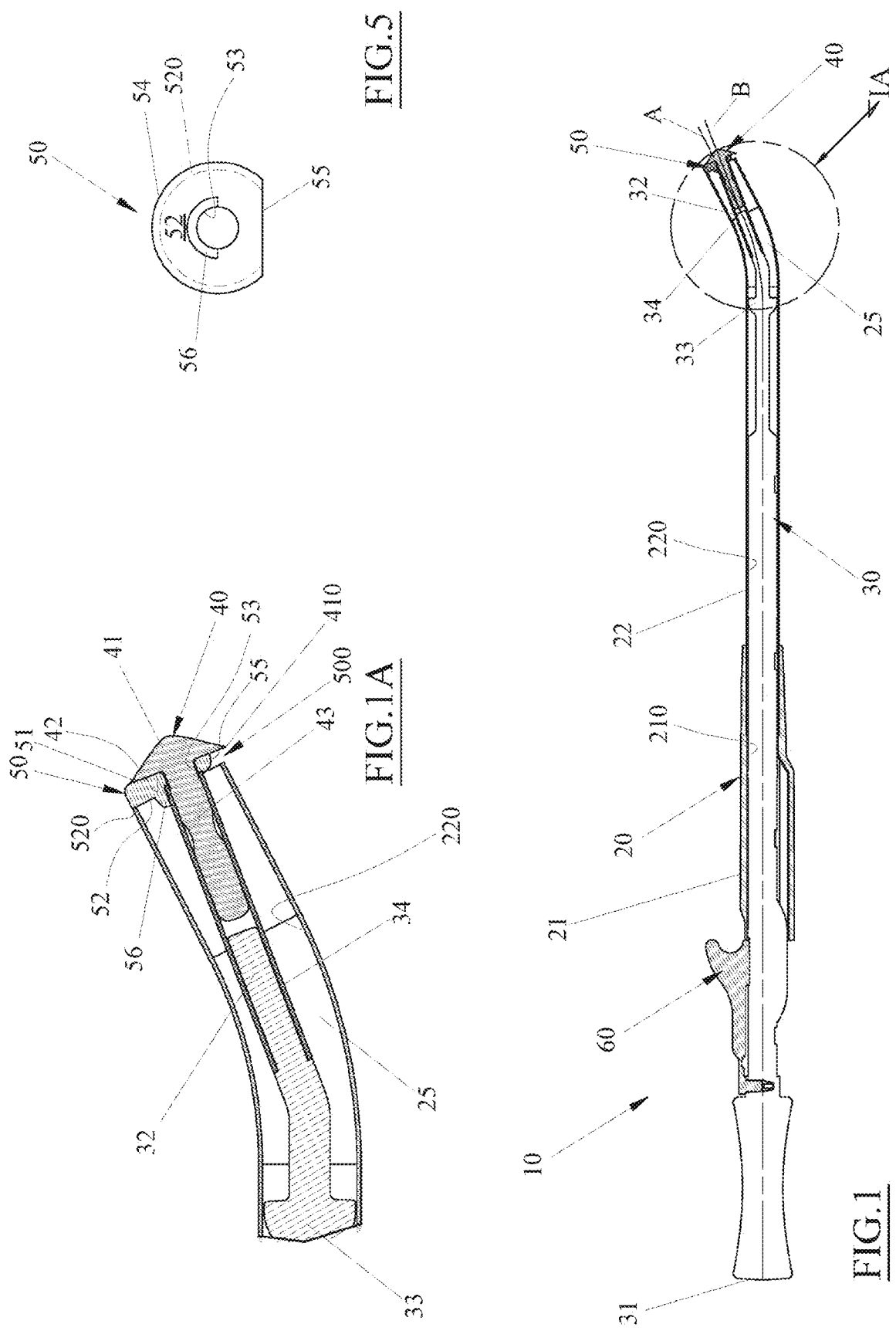
FIG. 1 is a longitudinal section view of a first embodiment of a surgical tool according to the invention, in a collection position.
FIG. 1A is an enlargement of detail IA of FIG. 1.
FIG. 5 is a front (back) view of a spacer element of a surgical tool according to the invention.

With particular reference to these figures, a surgical tool for scraping and collecting, e.g. manually, bone particles, i.e. shavings or chips/flakes of bone, is globally referred to as 10.

In this disclosure, the terms "lower" and "upper" are used in this description referring to the position of the surgical tool 10 in use configuration, wherein "lower" means facing the bone to be scraped and "upper" means facing the part opposite the bone to be scraped.

Furthermore, the terms "front or "distal" and "back" or proximal" have been used in the present description referring to the position of the surgical tool 10 with respect to the hand holding the tool, wherein "front" or "distal" means in a position furthest from the palm of the user's hand and "back" or "proximal" means in a position closest to the palm of the user's hand.

The surgical tool 10 comprises a handle 20 that can be held (at the back) by an operator.

The handle 20 has an elongated body provided with a longitudinal axis A.

For example, the opposite axial ends of the handle 20 are open.

The handle 20 comprises, at the back, a handgrip 21 adapted to be held by one hand of the operator and an opposite distal end is free.

A proximal end of the handgrip 21 defines the proximal end of the handle 20.

The handle 20 also comprises a cannula 22, which is attached at the front to the handgrip 21.

The cannula 22 axially extends the handgrip 21 (in the front direction).

A distal end of the handgrip 21 defines the distal end of the handle 20.

The cannula 22, in particular, has a proximal end fixed, for example snap-fitted or screwed or welded or otherwise, to the distal end of the handgrip 21 and a free opposite distal end.

The cannula 22, for example, has a constant transversal section (orthogonal to the longitudinal axis A) throughout its longitudinal extension.

For example, the cannula 22 has an inner chamber 220, which is substantially cylindrical (the term "cylindrical" meaning that its transversal section may be circular, as in the preferred example shown, or of any other shape).

The inner chamber 220 of the cannula 22 is axially prolonged in a backward direction from an inner cavity 210 of the handgrip 21, for example having the same shape and size as the inner chamber 220 of the cannula 22.

In practice, the handle 20 defines as a whole a hollow body having an axial cavity formed by the inner cavity 210 of the handgrip 21 and the inner chamber 220 of the cannula 22 joining.

In the example shown, the cannula 22 and the handgrip 21 are made of two separate bodies, but it is not excluded that they can be made as a single body.

Figures 2, 2A:
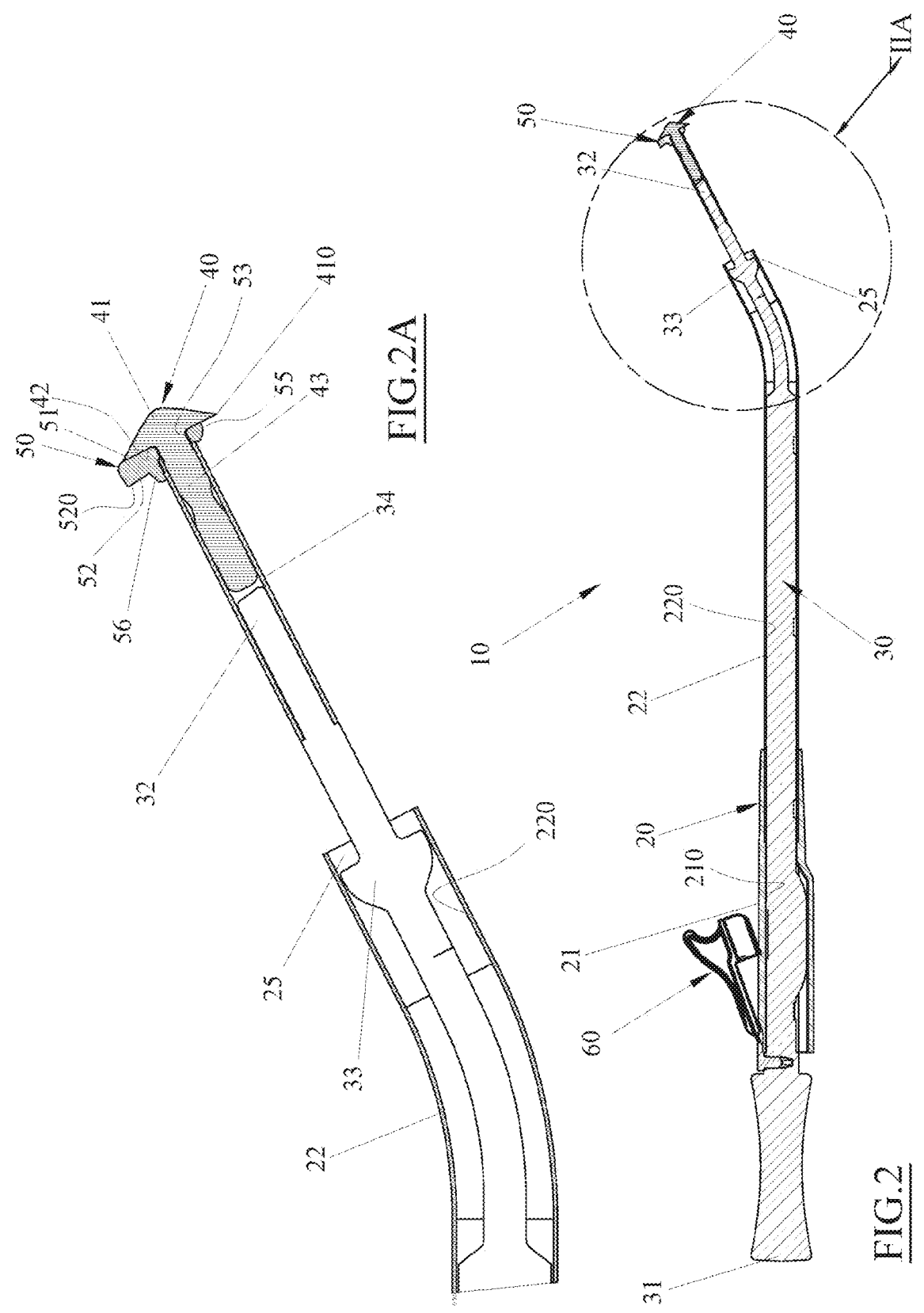
FIG. 2 is a longitudinal section view of the surgical tool of FIG. 1, in the discharge position.
FIG. 2A is an enlargement of detail IIA of FIG. 2.

In a first embodiment shown in FIGS. 1 and 2, the cannula 22 has a rectilinear portion, proximal to the proximal end (and ending at the back therewith) of the cannula itself, which has a rectilinear (coaxial) longitudinal axis, and a curved portion, proximal to the distal end of the cannula 22 (at a non-zero distance from it), which has a curved longitudinal axis (e.g. according to an arc of a circumference).

In such a first embodiment, the cannula 22 also has a further rectilinear portion, proximal to the distal end of the cannula itself (and terminating at the front therewith), which has a rectilinear (coaxial) longitudinal axis, tilted (at the top) with respect to the longitudinal axis of the rectilinear portion by an angle substantially between 20° and 40°, for example equal to 27°.

In practice, the curved portion of the cannula 22 is axially interposed between the rectilinear portion and the further rectilinear portion.

For example, the curvature of the cannula 22 is such that it curves at the top the distal end of cannula 22, i.e. it has an upper intrados and a lower extrados.

Figures 3, 3A:
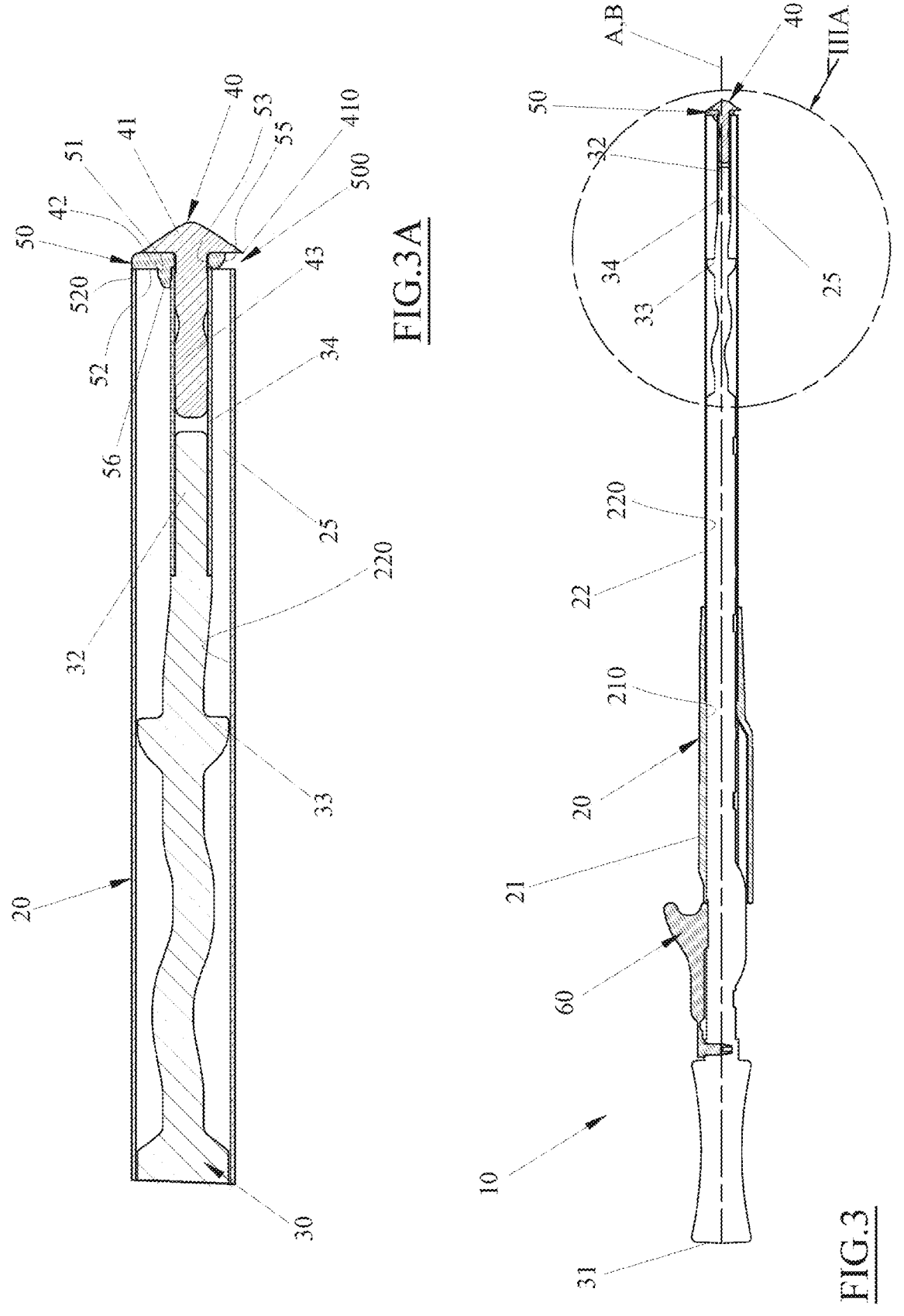
FIG. 3 is a longitudinal section view of a second embodiment of a surgical tool according to the invention, in a collection position.
FIG. 3A is an enlargement of detail IIIA of FIG. 3.
Figures 4, 4A:
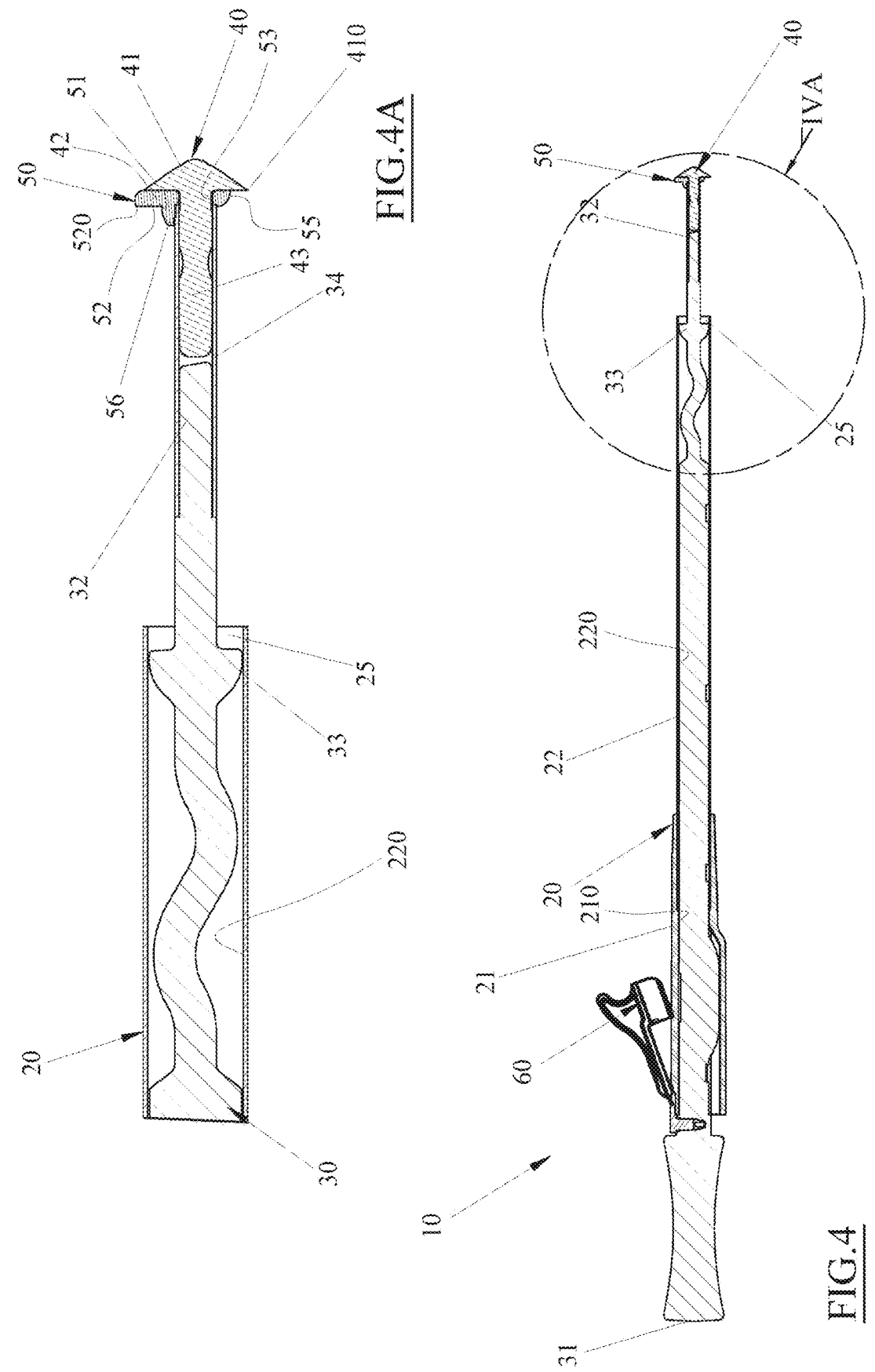
FIG. 4 is a longitudinal section view of the surgical tool of FIG. 3, in the discharge position.
FIG. 4A is an enlargement of detail IVA of FIG. 4.

In a second embodiment shown in FIGS. 3 and 4, the cannula 22 has a (totally) rectilinear longitudinal axis.

The distal end of the cannula 22, i.e. of the handle 20, is (completely) planar (and free from steps or notches).

The cannula 22 internally delimits a collection chamber 25, which is defined near the distal end thereof.

In particular, the distal end of the cannula 22 coincides with the distal end of the collection chamber 25.

The collection chamber 25 is defined internally by a distal portion of the inner chamber 220 of the cannula 22, i.e. it is delimited perimetrically by the (perimeter wall of) the cannula 22 and at the front by the distal end of the cannula 22 itself.

The collection chamber 25 has, as will be better described hereinafter, a variable volume, e.g. it has a proximal end which is (axially) movable with respect to the distal end.

The surgical tool 10 further comprises a stem 30, which is housed, at least partially, inside the handle 20, i.e. the handgrip 21 and/or the cannula 22.

The stem 30 is defined by an elongated body along a longitudinal axis B and is axially inserted inside the handle 20 (i.e. of the handgrip 21 and/or the cannula 22).

The stem 30 has a back end 31, which—for example—protrudes from the proximal (open) end of the handle 20, i.e.

of the handgrip 21, and an opposite front end 32 arranged near the distal end of the handle, i.e. of the cannula 22.

The stem 30 comprises at least one front end tract, provided with the front end 32 thereof, which is adapted to be contained within the collection chamber 25, with abundant radial clearance.

The collection chamber 25, in practice, is defined by a radial portion of the inner chamber 220 of the cannula 22 interposed between the (inner wall of the) cannula 22 and (the outer wall of the front end tract of) the stem 30.

The stem 30, furthermore, has an enlarged rear tract, which terminates at the back with a grip portion (again) defined externally at the back of (the handgrip 21 of) the handle 20 and provided with the back end 31.

The grip portion of the stem 30 is, for example, ergonomically shaped to be easily gripped by the user.

The back enlarged tract of the stem 30 is exactly radially received in the inner cavity 210 of the handgrip 21 (and/or at least one axial tract of the inner chamber 220 of the cannula 22).

On the front end tract of the stem 30 there is a shutter disc 33, which is exactly housed inside the inner chamber 220 of the cannula 22, so as to occlude (at the back) the collection chamber 25.

In practice, the collection chamber 25 is delimited perimetrically/radially by the (inner wall of the) cannula 22 and at the back by the shutter disc 33 of the stem 30, while it is open at the front at the distal end of the cannula 22 (i.e. of the handle 20).

The stem 30, e.g. at least or only its front end tract (except for the shutter disc 33), is elastically flexible (resilient), i.e. it is configured to be bendingly deformed, without being plastically deformed, and independently return elastically to its undeformed configuration.

For example, the stem 30, i.e. only the front end tract (except for the shutter disc 33) thereof, has a flexural rigidity (bending modulus) between 1500 MPa and 4500 MPa, preferably 2600 MPa.

Again, the stem 30, e.g. at least or only its front end tract (except for the shutter disc 33), is elastically extensible (preferably elongatable), i.e. it is configured to be tensile deformed, without being plastically deformed, and independently return elastically in its undeformed configuration.

For example, the stem 30, i.e. only the front end tract (except for the shutter disc 33) thereof, has an elastic (tensile) modulus, also called Young's modulus, of between 2000 MPa and 5000 MPa, preferably 3000 MPa.

The stem 30 (preferably in a single piece) is for example made of a plastic material.

The surgical tool 10 further comprises a blade 40 configured to scrape bone particles, e.g. in the form of bone shavings or chips/flakes.

The blade 40 is supported by the stem 30, near the front end 31 thereof.

The blade 40 has a rigidity (which is high, i.e. greater than the rigidity of the bone) such that it does not resonate during the scraping operation it is subjected to.

The blade 40 is generally made of metal, preferably stainless steel.

For example, the blade 40 is attached, preferably unseparatedly, to the front end 32 of the stem 30.

The blade 40 is arranged outside the handle 20 (i.e. the cannula 22 thereof).

In practice, the blade 40 is arranged at the front of the distal end (of the cannula 22) of the handle 20.

The blade 40 protrudes radially from the stem 30, for example by a radial tract having substantially the same width as the width of the collection chamber 25.

The blade 40 comprises a cap 41 provided with a sharpened (radial) scraping edge 410, for example facing downwards.

The scraping edge 410 (globally) has a circumferential longitudinal extension.

The scraping edge 410 is a free edge (in use) of the blade 40, i.e. protruding from the handle 20 (either axially or radially) or otherwise not in contact with it or with other elements of the surgical tool 10, preferably facing downwards with respect to the handle 20.

In the embodiment shown in FIGS. 1 and 2, the scraping edge 410 is arranged radially outwards from the extrados part of the curvature assumed by the cannula 22.

The blade 40 comprises a rear (or scraping) face 42, substantially planar, facing backwards (i.e., towards the distal end of the handle 20 and/or the cannula 22).

The rear face 42 is substantially orthogonal to the longitudinal axis B of the stem 30, or at least of a tract thereof proximal to its front end to which the blade 40 is attached.

The blade 40 further comprises a fastening tang 43, for example cylindrical or prismatic, which is derived from the cap 41 (in a single piece with it), for example from the rear face 42 thereof, with its axis orthogonal to the rear face 42.

The fastening tang 43 is configured to be firmly and rigidly fastened to the front end of the stem 30, for example by remaining firmly engaged thereon without any possibility of movement.

For example, the stem 30 includes a fastening tube 34 having a back end fitted on the front end of the stem 30 and fastened thereon, for example by crimping, and a front end fitted on the fastening tang 43 and fastened thereon, for example by crimping.

The surgical tool 10 further comprises a spacer 50, which is configured to be interposed between the rear face 42 of the blade 40 and the distal end of the collection chamber 25 (i.e. of the cannula 22).

The spacer 50 is made in a body separated from the blade 40 and the cannula 22 (and/or from the collection chamber 25).

Preferably, but not limited to, the spacer 50 is rigidly fastened to the stem 30 (and/or the blade 40).

In the example shown, the spacer 50 is rigidly fastened to the blade 40, for example fitted on the fastening tang 43 (with the interposition of the fastening tube 34 and/or of an end portion of the stem 30).

The spacer 50, globally, is such that it partially occludes the distal end of the collection chamber 25 leaving (open only) a lower passage opening 500 for introducing the bone particles scraped by the blade 40 into the collection chamber 25.

Such passage opening 500 is obtained by keeping at a distance, for at least a lower circumferential tract of the spacer 50, the lower portion of the rear face 42 of the blade 40 (provided with the scraping edge 410) from the (lower portion of) distal end of the collection chamber 25.

The spacer 50 is provided with a first (front) face 51 facing the blade 40 and in contact with the rear face 42 thereof and an opposite second face 52 facing the distal end of the collection chamber 25 (and the cannula 22), of which an upper circumferential contact portion 520 (lower than its entire circumferential perimeter) is intended to contact it.

In practice, the contact portion 520 is configured to contact the distal end of the collection chamber 25 by closing (at the top) the latter (as will be better described hereinafter).

The spacer 50 is basically shaped like a collar.

Preferably, the spacer 50—as shown schematically in FIG. 5—has an annular shape comprising a central hole 53 coaxial with the stem and/or the fastening tang 43 of the blade 40 and an asymmetrical outer perimeter provided with an upper circular portion 54 configured to define at the back the aforesaid contact portion 520 of the second face 52.

The outer perimeter of the spacer 50, moreover, is provided with a (lower) recess 55, having a radial dimension smaller than the radial dimension of the circular portion 54, which is adapted to be radially separated from the distal end of the collection chamber 25 (when the contact portion 520 defined in the circular portion 54 is in contact with the distal end of the collection chamber 25 itself).

The passage opening 500 is, in practice, delimited:

in the axial direction, at the front, by a (lower) portion of scraping edge 410 of the blade 40 and, at the back, by a circumferential (lower) portion of the distal end of the collection chamber 25 (facing and at a non-zero distance from the scraping edge 410 of the blade 40); and in the circumferential direction by the recess 55 of the spacer 50.

The axial width of the passage opening 500 is, substantially, equal to the axial thickness of the spacer 50 (at the circular portion 54, i.e. of the contact portion 520 thereof).

The circumferential width of the passage opening 500 is substantially equal to the (angular) width of the recess 55.

As an alternative to the foregoing, it is possible to provide that the spacer is arc-shaped having two opposite circumferential ends mutually placed at a non-zero predetermined circumferential distance and lower than the diameter of the portion of the stem 30 (and/or fastening tang 43 and/or fastening tube 34) that they embrace, wherein the passage opening 500 is delimited in the axial direction by a lower portion of the scraping edge 410 of the blade 40 (at the front) and by a circumferential portion of the distal end of the collection chamber 25 facing the scraping edge 410 (backwards) and in the circumferential direction by the circumferential ends of the spacer 50.

The spacer 50 further comprises an inner tang 56 axially protruding from the second face 52 thereof, which is configured to embrace, at least partially (i.e. preferably only in the upper portion), an (upper) portion of the fastening tang 43 and/or the fastening tube 34 and/or the stem 30.

The maximum radial dimension of the inner tang 56 is (abundantly) smaller than the inner diameter of the collection chamber 25, so as to be inserted therein (with abundant radial clearance) inside the collection chamber 25, when the second face 52 of the spacer 50 is in contact (by its contact portion 520) with the distal end of the collection chamber 25 itself.

The inner tang 56, for example, has a radial thickness increasing from the free back end to the back end that joins to the second face 52, defining a guide ramp.

For example, the spacer 50 is substantially rigid (non-deformable), e.g. made of plastic or metal.

Preferably, the collection chamber 25, i.e. the handle 20, and the stem 30 are mutually movable in axial sliding, alternatively between:

a collection position of the collection chamber 25, wherein the second face 52 of the spacer 50 is in contact (with its contact portion 520) with the distal end of the collection chamber 25 and the collection chamber 25 is accessible (i.e., open to the outside) only through the passage opening 500 defined by the spacer 50, and a discharge position, wherein the second face 52 of the spacer 50 (and also the contact portion 520 thereof) is distal from the distal end of the collection chamber 25 by releasing the same, i.e. opening it axially (at its free end), i.e. increasing the opening area of the collection chamber 25 with respect to the opening area thereof when the collection chamber 25 and the stem 30 are in the collection position.

Preferably, the stem 30 is slidably movable within the handle 20, by means of a prismatic-type connection (i.e. without possibility of axial rotation).

As mentioned above, the collection chamber 25 has a variable volume, i.e. it has a maximum volume when the stem 30 and the collection chamber 25 are in the collection position and has a minimum volume when the stem 30 and the collection chamber 25 are in the discharge position.

In fact, when the stem 30 and the collection chamber 25 are in the collection position, the shutter disc 33 is placed at a maximum non-zero distance from the distal end of the collection chamber 25, for example greater (even twofold or threefold) than the inner diameter of the cannula 22, and when the stem 30 and the collection chamber 25 are in the discharge position, the shutter disc 33 is placed at a minimum distance (lower than the maximum distance) from the distal end of the collection chamber 25, wherein for example such minimum distance is substantially zero or in any case lower than the inner diameter of the cannula 22.

In practice, the shutter disc 33 (defining the proximal end of the collection chamber 25) is such as to act as a plunger for discharging the bone chips collected in the collection chamber when the stem 30 and the collection chamber 25 are brought from the collection position to the discharge position, operating a back pushing action on the bone chips towards the distal end of the collection chamber 25 (released from the closure operated by the blade 40) from which they exit.

When the stem 30 and the collection chamber 25 are brought from their discharge position to the collection position, the inner tang 56 of the spacer 50, especially in the embodiment shown in FIGS. 1 and 2, acts as a guide ramp (creeping against the distal end of the collection chamber) to take the spacer 50 to its correct position, wherein the second face 52 of the spacer 50 is in contact (with its contact portion 520) with the distal end of the collection chamber 25 leaving only the passage opening 500 open.

The surgical tool 10 further comprises a locking element 60, which is configured to temporarily and/or removably mutually lock the stem 30 and the collection chamber 25 at least in their collection position.

It is not excluded that the locking element 60 may be configured to mutually lock the stem 30 and the collection chamber 25 selectively in the collection position and discharge position.

The locking element 60 comprises, for example, a harpoon (rotatably) associated with the back end 31 of the stem 30, which is movable between an engagement position of a seat made at (the rear end 31 of) the stem 30 and a disengagement position thereof.

When the stem 30 and the collection chamber 25 are in their collection position, the seat is arranged outside (at the back of) the handle 20 and is engageable or disengageable by the locking element 60.

When the locking element 60 is in the engaged position (and the stem 30 and the collection chamber 25 are in their collection position), the locking element 60 prevents any sliding movement between the stem 30 and the collection chamber 25 (abutting against the back end of the handle 20).

When the locking element 60 is in the engaged position, the locking element 60 allows the sliding movement between the stem 30 and the collection chamber 25, allowing them to reach their discharge position.

In light of the above, the operation of the surgical tool 10 is as follows.

The surgical tool 10, with the stem 30 and the collection chamber 25 in their collection position, is configured to be used to obtain bone particles (in the form of chips or shavings) and collect them, once separated from the bone to which they belong, within the collection chamber 25.

In order to carry out this operation, it is sufficient to hold the handgrip 21 of the surgical tool 10 and lead the scraping edge 410 of the blade 40 into contact with a bone surface.

As the surgical tool 10 has a curved cannula 22, as illustrated in the embodiment shown in FIGS. 1 and 2, the relative position between the handgrip 21 and the bone further facilitates reaching the scraping area and the scraping operations themselves.

In order to scrape a bone particle it is sufficient to scrape with the scraping edge 410 of the blade in contact with the surface of a bone to be scraped, in the backward (rectilinear) direction, i.e. orthogonal to the rear face 42 of the blade 40 in the direction from the blade 40 towards the handgrip 21.

The bone particle produced by the blade 40 is pushed (from the rear face 42 of the blade itself) into the collection chamber 25 through the passage opening 500 defined by the spacer 50.

During this scraping action, moreover, the stem 30 is stressed in bending (by the constraint reaction exerted by the bone), and bends (in contrast to the flexural elasticity of the stem 30) upwards (such bending is however limited, for example by the feedback exerted by the inner wall of the cannula 22 against the inner tang 56).

As an alternative or in addition, during such a scraping action, the stem 30 is tensile stressed (by the restraint reaction exerted by the bone), and extends (in contrast to the axial elasticity of the stem itself) axially (tending to detach the second face 52 of the spacer 50 from the distal end of the collection chamber 25).

When the constraint reaction of the bone is overcome by the tensile action exerted by the operator and/or the elastic reaction (flexural and/or axial) exerted by the stem 30, the bone particle separates from the bone, for example by a shearing action (exerted by the scraping edge 410 of the blade 40), and is forced to enter the collection chamber 25 where it is stored.

In practice, it has been observed that the flexural and/or axial elasticity of the stem 30 is such as to produce an impulsive shear force that allows (the scraping edge 410 of) the blade 40 to enhance the detachment of the bone particles from the scraped bone.

Once the desired amount of bone particles has been collected, for example by several consecutive scraping actions—as described above—, the operator may discharge the collected bone particles into the collection chamber 25, for example into a suitable collection container.

To do so, it is sufficient to bring the stem 30 and the collection chamber 25 to their discharge position and to let the collected bone particles pass through the distal end of the collection chamber 25 which is disengaged from the blade 40.

The invention thus conceived is susceptible to several modifications and variations, all falling within the scope of the inventive concept.

Moreover, all the details can be replaced by other technically equivalent elements.

In practice, the materials used, as well as the contingent shapes and sizes, can be whatever according to the requirements without for this reason departing from the scope of protection of the following claims.

The invention claimed is:

1. A surgical tool for scraping and collecting bone particles, comprising:

a handle provided with a handgrip;

a collection chamber having an end proximal to the handgrip and a free distal end;

a stem at least partially arranged inside the collection chamber;

a blade fixed to a front end of the stem, wherein the blade protrudes radially from the stem and is axially arranged outside the collection chamber near the distal end thereof; and a spacer interposed between a rear face of the blade and the distal end of the collection chamber, wherein the spacer defines a passage opening for introducing the bone particles scraped by the blade into the collection chamber, maintaining at a predetermined non-zero axial distance, for at least a circumferential tract thereof, the rear face of the blade from the distal end of the collection chamber, wherein the spacer is a body separated from the blade, the stem, and the handgrip.

2. The surgical tool according to claim 1, wherein the spacer is rigidly fixed to the blade and is provided with one first face facing the blade and in contact with it and a second face facing the distal end of the collection chamber and intended to contact it by a contact portion of the second face.

3. The surgical tool according to claim 1, wherein the spacer has an annular shape with a first face and a second face, the spacer comprising a central hole coaxial with the stem and an asymmetrical outer perimeter provided with a circular portion configured to define a contact portion of the second face, wherein the contact portion is configured to contact the distal end of the collection chamber, and a recess adapted to be radially separated from the distal end of the collection chamber, wherein the passage opening is delimited, in an axial direction, by a portion of a scraping edge of the blade and by a circumferential portion of the distal end of the collection chamber and, in a circumferential direction, by the recess of the spacer.

4. The surgical tool according to claim 1, wherein the distal end of the collection chamber is planar and free from steps or notches.

5. The surgical tool according to claim 1, wherein the collection chamber has a curved longitudinal extension along a curved line with an only curvature, the passage opening being arranged at an extrados area of the distal end of the collection chamber.

6. The surgical tool according to claim 1, wherein the stem is elastically flexible.

7. The surgical tool according to claim 1, wherein the stem can be elastically elongated.

8. The surgical tool according to claim 2, wherein the collection chamber and the stem are mutually movable sliding between a collection position of the collection chamber, wherein the second face of the spacer is in contact with the distal end of the collection chamber and the collection chamber is accessible from outside only by the passage opening defined by the spacer, and a discharge position, wherein the second face of the spacer is distal from the distal end of the collection chamber discharging it.

9. The surgical tool according to the claim 8, which comprises a locking element configured to temporarily lock the stem and the collection chamber at least in the collection position thereof.

10. A surgical tool for scraping and collecting bone particles, comprising:
  a handle provided with a handgrip;
  a collection chamber having an end proximal to the handgrip and a free distal end;
  a stem at least partially arranged inside the collection chamber;
  a blade fixed to a front end of the stem, wherein the blade protrudes radially from the stem and is axially arranged outside the collection chamber near the distal end thereof, and
  a spacer interposed between a rear face of the blade and the distal end of the collection chamber, wherein the spacer defines a passage opening for introducing the bone particles scraped by the blade into the collection chamber, maintaining at a predetermined non-zero axial distance, for at least a circumferential tract thereof, the rear face of the blade from the distal end of the collection chamber,
  wherein the spacer has an annular shape with a first face and a second face, the spacer comprising
  a central hole coaxial with the stem and
  an asymmetrical outer perimeter provided with
a circular portion configured to define a contact portion of the second face, wherein the contact portion is configured to contact the distal end of the collection chamber, and
  a recess adapted to be radially separated from the distal end of the collection chamber,
  wherein the passage opening is delimited, in an axial direction, by a portion of a scraping edge of the blade and by a circumferential portion of the distal end of the collection chamber and, in a circumferential direction, by the recess of the spacer.

* * * * *